United States Patent [19]

Seligson et al.

[11] Patent Number: 4,789,664

[45] Date of Patent: Dec. 6, 1988

[54] FOOD COMPOSITIONS WITH SUPERIOR BLOOD CHOLESTEROL LOWERING PROPERTIES

[75] Inventors: Frances H. Seligson, Fairfield; John E. Hunter, Cincinnati; Albert H. St. Clair, Blue Ash, all of Ohio

[73] Assignee: The Procter & Gamble Company, Cincinnati, Ohio

[21] Appl. No.: 120,459

[22] Filed: Nov. 13, 1987

Related U.S. Application Data

[63] Continuation-in-part of Ser. No. 944,148, Dec. 19, 1986, abandoned.

[51] Int. Cl.$^4$ .................... A01N 9/00; A61K 31/70
[52] U.S. Cl. ......................... 514/23; 514/824; 426/574; 426/580; 426/601; 426/607; 426/611
[58] Field of Search ............... 514/23, 824; 426/574, 426/580, 601, 601, 611

[56] References Cited

U.S. PATENT DOCUMENTS

| | | | |
|---|---|---|---|
| 3,600,186 | 8/1971 | Mattson et al. | 426/611 |
| 3,814,823 | 6/1974 | Yang et al. | 426/802 |
| 3,840,679 | 10/1974 | Liepa et al. | 426/802 |
| 3,935,319 | 1/1976 | Howard | 426/601 |
| 3,954,976 | 5/1976 | Mattson et al. | 514/23 |
| 4,001,441 | 1/1977 | Liepa | 426/802 |
| 4,005,195 | 1/1977 | Jandacek | 426/658 |
| 4,005,196 | 1/1977 | Jandacek et al. | 514/53 |
| 4,034,083 | 7/1977 | Mattson | 514/53 |
| 4,186,218 | 1/1980 | Gomi et al. | 530/378 |
| 4,241,054 | 12/1980 | Volpenhein et al. | 536/115 |
| 4,264,583 | 4/1981 | Jandacek | 514/877 |
| 4,368,213 | 1/1983 | Hollenbach et al. | 426/612 |
| 4,382,924 | 5/1983 | Berling et al. | 426/601 |
| 4,447,461 | 5/1984 | Loos et al. | 426/802 |
| 4,461,782 | 7/1984 | Robbins et al. | 426/549 |
| 4,596,714 | 8/1986 | Brabbs | 426/633 |
| 4,626,441 | 12/1986 | Wolkstein | 426/613 |
| 4,686,205 | 8/1987 | Betz et al. | 514/25 |

FOREIGN PATENT DOCUMENTS 207070 2/1984 German Democratic Rep. .

OTHER PUBLICATIONS

Tomita et al., "Quality Improvement of Meat Paste Product", Japan Tokkyo Koho 79, 28,464 (Sep. 1979).

European Patent Application O 233 856 of Bernhardt, published Aug. 26, 1987.
Perotti, "Sucrose Esters and Food Products", Industrie Alimentari 14 (1), pp. 77–81 (1975).
Fukuda, "Effects of Surface Active Agents on Meat Paste Prepared from Frozen Mackerels", Aomori–Ken Suisanbutsu Kako, pp. 33–41 (1977).
Fallat et al., "Short Term Study of Sucrose Polyester, a Nonabsorbable Fat-Like Material, as a Dietary Agent for Lowering Plasma Cholesterol", The American Journal of Clinical Nutrition 29, Nov. 1976, pp. 1204–1215.
Mattson et al., "The Effect of a Nonabsorbable Lipid, Sucrose Polyester, on the Absorption of Dietary Cholesterol by the Rat", The Journal of Nutrition, vol. 106, No. 6, Jun. 1976.
European Patent Application 0 236 288 of Bernhardt, published Sep. 9, 1987.

Primary Examiner—Ronald W. Griffin
Attorney, Agent, or Firm—Gary M. Sutter; Eric W. Guttag; Richard C. Witte

[57] ABSTRACT

The invention relates to foods that contain both sucrose polyesters and vegetable proteins. The foods are effective in reducing blood plasma cholesterol levels. In particular, the invention is a fat-containing and protein-containing food composition comprising fat ingredients, protein ingredients, and non-fat and non-protein ingredients; wherein at least 1 gram per serving of the total fat consists essentially of a sucrose fatty acid ester having at least 4 fatty acid ester groups, each fatty acid having from about 8 to about 22 carbon atoms; and wherein at least 1.5 grams per serving (by protein content) of the total protein comprises vegetable protein.

The invention is also a method for lowering plasma cholesterol levels comprising administering to a human susceptible to or afflicted with hypercholesterolemia the present food compositions, wherein the compositions are administered to provide at least about 0.5% sucrose fatty acid ester in the daily diet (dry weight basis) and a daily dietary ratio of vegetable protein to animal protein of at least about 50:50. Importantly, the level of high density lipoproteins in the plasma is maintained while the level of total cholesterol is lowered. The method is also effective in lowering plasma triglyceride levels.

24 Claims, No Drawings

FOOD COMPOSITIONS WITH SUPERIOR BLOOD CHOLESTEROL LOWERING PROPERTIES

CROSS REFERENCE TO RELATED APPLICATION

This application is a continuation-in-part of U.S. application Ser. No. 944,148, filed Dec. 19, 1986, now abandoned.

FIELD OF THE INVENTION

This invention relates to foods that contain a combination of sucrose polyester and vegetable protein. The foods are effective in reducing blood cholesterol levels.

BACKGROUND OF THE INVENTION

A 1984 National Institutes of Health consensus development conference concluded that high blood cholesterol levels are a major cause of coronary artery disease and that the risk of heart attacks would be reduced by lowering definitely elevated blood cholesterol levels. It also recommended (a) lowering the average blood cholesterol level of the entire population, (b) a national campaign to educate consumers and health professionals why and how to lower high blood cholesterol levels, and (c) intensified development of products to facilitate blood cholesterol reduction.

Medicines for lowering blood cholesterol often have undesirable side effects. As currently practiced, most diet-based treatments for lowering cholesterol also have drawbacks. For instance, they require major changes in eating habits and a high level of nutritional knowledge and dietary training. These drawbacks severely limit the effectiveness of current diet-based approaches.

Therefore, there is a need for a method of lowering blood cholesterol without the use of drugs and without the need for major changes in eating habits.

Several references disclose the use of sucrose polyesters in food compositions. U.S. Pat. No. 3,600,186 to Mattson et al., issued Aug. 17, 1971, discloses low calorie, fat-containing food compositions in which at least a portion of the triglyceride content is replaced by a polyol fatty acid ester, the polyol fatty acid ester having at least four fatty acid ester groups with each fatty acid having from 8 to 22 carbon atoms. Sucrose polyesters are preferred polyol fatty acid esters.

U.S. Pat. No. 4,005,195 to Jandacek, issued Jan. 25, 1977, discloses sucrose polyesters used in food compositions to treat and/or prevent hypercholesterolemia. It is disclosed that sucrose polyesters have a cholesterol-lowering effect in the body. A cooking fat and a plastic shortening are described.

It is an object of the present invention to provide a method for reducing blood cholesterol levels without the use of drugs and without major dietary changes.

It is another object of the present invention to provide food compositions that, when eaten on a regular basis, are effective at reducing blood cholesterol levels.

It is a further object of the present invention to make food compositons that have the enhanced blood cholesterol lowering benefits of the combination of sucrose polyester and vegetable protein.

These and other objects of the invention will become evident from the disclosure herein.

All percentages are by weight unless otherwise defined.

SUMMARY OF THE INVENTION

The invention relates to foods that contain both sucrose polyesters and vegetable proteins. The foods are effective in reducing blood cholesterol levels. In particular, the invention is a fat-containing and protein-containing food composition comprising fat ingredients, protein ingredients, and non-fat and non-protein ingredients; wherein at least 1 gram per serving of the total fat consists essentially of a sucrose fatty acid ester having at least 4 fatty acid ester groups, each fatty acid having from about 8 to about 22 carbon atoms; and wherein at least 1.5 grams per serving (by protein content) of the total protein comprises vegetable protein.

The invention is also a method for lowering human blood plasma cholesterol levels comprising administering to a human susceptible to or afflicted with hypercholesterolemia the present food compositions, wherein the compositions are administered to provide at least about 0.5% sucrose fatty acid ester in the daily diet (dry weight basis) and a daily dietary ratio of vegetable protein to animal protein of at least about 50:50. Importantly, the level of high density lipoproteins in the plasma is maintained while the level of cholesterol is lowered. The method is also effective in lowering plasma triglyceride levels.

DETAILED DESCRIPTION OF THE INVENTION

The present development affords a preferred and convenient dietary means of reducing blood plasma cholesterol. It does this without the undesirable side effects associated with the use of cholesterol-lowering drugs, without a requirement for nutritional knowledge, and without a major change in eating habits. The development also provides a means for reducing the intake of fat and animal protein by replacing them with significant quantities of sucrose polyester and vegetable protein in a highly palatable form.

A. Food Compositions

These benefits are achieved by the use of a fat-containing and protein-containing food composition comprising fat ingredients, protein ingredients, and nonfat and non-protein ingredients; wherein at least 1 gram per serving of the total fat consists essentially of a particular sucrose fatty acid ester (sucrose "polyester"), and wherein at least 1.5 grams per serving (by protein content) of the total protein comprises vegetable protein.

Vegetable protein is combined with sucrose polyester in the present food compositions at levels which when consumed on a regular basis will significantly lower plasma cholesterol without other dietary change. Preferably, at least 3 grams of the total fat of the present food compositions consists essentially of the sucrose fatty acid ester, and at least 4.5 grams of the total protein comprises vegetable protein (by protein content). More preferably, at least 5 grams of the total fat consists essentially of the sucrose fatty acid ester and at least 8 grams of the total protein comprises vegetable protein, and most preferably from 5 grams to about 20 grams of the total fat consists essentially of the sucrose fatty acid ester.

The development is designed to achieve cholesterol lowering simply from daily eating of a single item or combination of food items containing the sucrose polyester and vegetable protein to attain the desired sucrose polyester and vegetable protein intakes. Cholesterol lowering results even if other parts of the diet are hypercholesterolemic. However, the present food compositions provide a method for converting a normally hypercholesterolemic diet to a hypocholesterolemic diet in a very convenient, highly palatable manner. For example, when an entree prepared according to the present invention is compared with a similar entree containing moderately lean ground beef, the levels of calories, saturated fat, cholesterol and animal protein are reduced, and vegetable protein intake is increased.

"Grams of vegetable protein," as used herein, is calculated as the weight of the protein content of the vegetable protein source, not the weight of the whole source material. For example, a 50 gram sample of tofu contains about 3.9 grams of vegetable protein.

The food compositions of this invention can be any foods that combine vegetable protein and sucrose polyester at levels effective at reducing plasma cholesterol. Meat analogs can be made from vegetable protein and sucrose polyester, for example, beef slices, chunks and pieces, ground beef, ham, bacon, beef jerky, poultry, fish and shellfish. The vegetable protein takes the place of all or part of the animal protein, and sucrose polyester replaces all or part of the triglyceride fat. The analogs can be used in frozen dinners, as entrees, or in jarred or canned meals.

Vegetable protein products per se can be made, which contain added sucrose polyester. Examples include tofu made with soy protein and sucrose polyester. Nut spread such as peanut butter and protein spreads can be made, with the oil replaced by sucrose polyester. Other products include imitation nuts and vegetable product beverages.

Dairy-type products are another example of the present food composition. These include milk, dairy beverages, cheese, puddings and other dairy desserts, and ice cream and other frozen desserts. The casein in these compositions is replaced by vegetable protein and the milkfat is replaced by sucrose polyester.

Other examples are baked goods supplemented with soy protein and in which a protein or all of the fat is replaced by sucrose polyester. The baked goods can be in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other possible baked goods include breads and rolls, crackers, pretzels, pancakes, waffles, ice cream cones and cups, yeast-raised baked goods, pizzas and pizza crusts, baked farinaceous snack foods, and other baked salted snacks.

Serving size varies with the type of food composition. A standard text which discloses the serving size of most foods is Pennington & Church, *Food Values of Portions Commonly Used*, 14th Ed., Harper & Row, New York (1985), incorporated by reference herein. Serving size is also generally indicated on the container of packaged foods. Table 1 below lists the serving sizes of some typical foods. The list is not meant to be comprehensive or to exclude other foods.

TABLE 1

| Food | Serving Size (g./Serving) | Food | Serving Size (g./Serving) | Food | Serving Size (g./Serving) |
|---|---|---|---|---|---|
| Cereals, cooked: oatmeal | 175 | Desserts: cupcakes | 42 | whole wheat bread | 28 |
| Cereals, ready to eat | 28 | cookies chocolate | 21 64 | white bread w/buttermilk | 28 |
| Cheese | 28 | chip cookies | | cheese crackers | 43 |
| Cottage cheese, creamed | 210 | chocolate brownies | 46 | French toast blueberry | 67 40 |
| Cottage cheese, low fat | 226 | Danish donuts | 37 42 | muffin brown & | 28 |
| Chips and snacks: | | cakes | 50 | serve rolls | |
| tortilla chips | 28 | ice cream | 133 | corn tortilla | 30 |
| corn chips | 28 | pie | 118 | Infant foods: | |
| Pringle's potato chips | 28 28 | sherbert, orange sweet roll | 193 28 | high meat-cheese dinner (1 jar) | 128 |
| Combination foods: | | turnover vanilla pudding | 84 125 | formula | 120 |
| chicken pie (8 oz.) | 227 | Fast foods: | | Meat analogs: | |
| frozen dinners | | beef burrito | 184 | breakfast links (5) | 68 |
| beef (11 oz.) | 312 | cheeseburger | 104 | | |
| fried chicken (11 oz.) | 312 | vanilla shake hot dog | 282 99 | hamburger, 1 patty | 85 |
| macaroni & cheese (12½ oz.) | 354 | onion rings pizza | 85 282 | rib roast (2 slices) | 106 |
| meatloaf (10¾ oz.) | 305 | Fish analogs (3½ oz.) | 100 | sirloin steak T-bone | 125 95 |
| Salisbury steak (16 oz.) | 454 | Flour & grain products: | | bacon, 1 slice ham | 21 100 |
| turkey (11½ oz.) | 454 | Bisquick mix | 56 | pork sausage | 100 |
| spaghetti w/ meatballs & tomato sauce | 209 | soybean flour pancakes | 100 112 | 2 patties veal cutlet 3½ oz. | 100 |
| Meat Analogs | | Milk, 1 cup | 244 | Sauces: | |
| luncheon meats, franks, sandwich | | Milk, soybean 1 cup Milk beverages: | 263 | sour cream stroganoff sauce | 52 80 |
| spreads: | | choc., 1 cup | 250 | Soups (1 cup): | |
| bologna, 1 slice | 28 | eggnog, 1 cup instant | 254 276 | bean w/bacon chicken noodle | 253 241 |

TABLE 1-continued

| Food | Serving Size (g./Serving) | Food | Serving Size (g./Serving) | Food | Serving Size (g./Serving) |
|---|---|---|---|---|---|
| frankfurter, 1 frank | 45 | breakfast w/whole milk 1 cup | | cream of mushroom | 248 |
| sliced ham, 1 slice | 28 | milkshake, chocolate | 300 | chili beef | 250 |
| honey loaf, 1 slice | 28 | yogurt, 1 cup | 227 | clam chowder | 248 |
| salami, 1 slice | 23 | Peanut butter (2 T.) | 32 | tomato | 248 |
| sandwich spread (1 oz.) | 28 | Poultry analogs (3½ oz.) | 100 | Special dietary foods: breakfast bar liquid meal, all types | 41 403 |

According to the present invention, the foods disclosed in Table 1 will have all or a portion of the total fat replaced by sucrose polyester, and all or a portion of the total protein replaced by vegetable protein.

In addition to serving size, the Pennington & Church text also discloses the protein and fat contents of foods, for example: cookies—1.5 g. protein, 3.3 g. fat; ice cream—4.8 g. protein, 14.3 fat; cheeseburger—14 g. protein, 13 g. fat; whole wheat bread—2.5 g. protein, 1 g. fat; and breakfast bar—6 g. protein, 11 g. fat.

B. Method of Lowering Blood Plasma Cholesterol

The present invention is also a method for lowering plasma cholesterol in humans susceptible to or inflicted with hypercholesterolemia by administering the present food compositions.

The food compositions are administered to provide at least about 0.5% sucrose fatty acid ester in the daily diet (dry weight basis) and a daily dietary ratio of vegetable protein to animal protein of at least about 50:50. Preferably, at least about 2.5% sucrose fatty acid ester is administered in the daily diet (dry weight basis). This preferred amount is equivalent to consuming at least about 5.5 g of sucrose polyester and at least about 8 g of vegetable protein per day, per 1000 kcal. of total daily energy intake. Therefore, it is preferred that the present food compositions have a ratio of vegetable protein to sucrose fatty acid ester of at least 1.25 to 1, more preferably at least 1.35 to 1, and most preferably at least 1.45 to 1.

These amounts of sucrose ester and vegetable protein can be administered by ingestion of a single food item or a combination of food items. Table 2 lists examples of the optimum intake of sucrose polyester and vegetable protein from the present food compositions, as a function of the total number of kilocalories of energy intake per day:

TABLE 2

| Energy Intake (kcal./day) | SPE (g./day) | Vegetable Protein (g./day) |
|---|---|---|
| 1000 | 5.5 | 8 |
| 1200 | 6.6 | 10 |
| 1600 | 8.8 | 13 |
| 2000 | 11.0 | 16 |
| 2400 | 13.2 | 19 |
| 2800 | 15.4 | 22 |
| 3200 | 17.6 | 26 |

Importantly, it has been found that while the method of the present invention is effective in reducing plasma total cholesterol levels, the method also maintains the level of high density lipoprotein (HDL) in the plasma. HDL is thought to reduce the deposition of cholesterol in the vascular system.

The invention is additionally a method for lowering plasma triglyceride levels in humans susceptible to or afflicted with hyperlipidemia by administering the present food compositions, at the same levels administered for lowering cholesterol levels.

The number of servings per day required to achieve the benefits of the present invention will depend on the total dietary energy intake per day, and the sucrose polyester and vegetable protein levels in the food compositions. Examples in Table 3 illustrate how intakes will change when 100 g. beef analog replaces 100 g. lean ground beef in 1200, 2000 and 2800 calorie diets containing 400 mg. cholesterol and a typical calorie distribution of protein—16%, carbohydrate—47%, and fat—37%. The beef analog is prepared as in Example 1.

TABLE 3

Effect of Daily Replacement of One Serving of Lean Ground Beef with Vegetable Protein/Sucrose Polyester Beef Analog on Total Daily Nutrient Intakes at Three Calorie Levels

| Comparison | 1200 calories | | 2000 calories | | 2800 calories | |
|---|---|---|---|---|---|---|
| | Beef | Analog | Beef | Analog | Beef | Analog |
| Total Calories | 1200 | 1050 | 2000 | 1850 | 2800 | 2650 |
| Pro, % | 16 | 14 | 16 | 15 | 16 | 15 |
| CHO, % | 47 | 55 | 47 | 55 | 47 | 50 |
| Fat, % | 37 | 31 | 37 | 33 | 37 | 35 |
| Pro, g | 48 | 38 | 80 | 70 | 112 | 102 |
| CHO, g | 141 | 145 | 250 | 254 | 329 | 333 |
| Fat, g | 49 | 36 | 82 | 69 | 115 | 102 |
| Cholesterol, mg | 400 | 330 | 400 | 330 | 400 | 330 |
| Animal:Vegetable Protein Ratio | 70:30 | 22:78 | 70:30 | 44:56 | 70:30 | 52:48 |
| Vegetable Pro, g | 14 | 29 | 24 | 39 | 34 | 49 |
| Animal Pro, g | 34 | 9 | 56 | 31 | 78 | 53 |
| Sucrose Polyester, g | 0 | 18 | 0 | 18 | 0 | 18 |

C. The Vegetable Protein

The present food compositions contain at least 1.5 grams per serving (by protein content) of vegetable protein. Suitable vegetable protein sources are soybeans, safflower seed, corn, oats, peanuts, wheat, sunflower seed, cottonseed, coconut, rapeseed, sesame seed, leaf proteins, single cell proteins such as yeast, and the like.

Generally, the vegetable protein source prior to use is placed in a relatively pure form, i.e. containing at least about 40% protein. Thus, for example, if the protein source is soybeans, the soybeans can be dehulled and solvent extracted, preferably with hexane, to remove the oil therefrom. The resulting oil-free soybean meal contains about 50% protein.

The soybean meal can be processed in a known manner to remove carbohydrates and obtain products with higher levels of protein, for example, soy protein concentrates containing about 70% protein or soy protein isolates containing about 95% or more protein. In turn, a variety of suitable processes can be employed to convert the soybean meal, concentrate, isolate or other edible protein bearing materials into suitable texturized edible protein fibers or meat analogs.

Suitable materials can be added to the vegetable protein or it can undergo various processes to enhance its palatability and biological effectiveness, while still maintaining its cholesterol lowering benefit. For example, the vegetable protein can be subjected to a process such as moist heat treatment to inactivate or remove antinutritional factors such as trypsin inhibitors, goitrogens, hemoglutins, or estrogenic factors. These factors reduce the biological value of the vegetable proteins.

Vegetable protein typically is of lower biological quality than animal protein because it lacks essential amino acids. Hence, protein quality can be improved by correcting the amino acid balance. U.S. Pat. Nos. 3,878,305 and 3,952,115 to Damico et al. describe a method for correcting sulfur-containing amino acid deficiency in vegetable proteins while maintaining palatability. The vegetable proteins are fortified with selected N-acyl derivatives of the L stereoisomeric form of such sulfur-containing amino acids. U.S. Pat. No. 4,379,177 to McCoy et al. discloses improved amino acid food additives for fortifying vegetable proteins. The additives comprise a uniform dehydrated cocrystalline matrix of (1) an amino acid material, preferably a salt of an amino acid material, and (2) an effective amount of a soluble edible cocrystallizer material, preferably sodium chloride. The improved amino acid food additive is better-tasting, more stable and less hygroscropic than the free amino acid material alone.

A preferred process for making a meat analog from vegetable protein is disclosed in U.S. Pat. No. 3,814,823 to Yang. The process involves forming a protein mix containing a heat-coagulable protein, adjusting the moisture content of the protein mix to form a wet mix having a moisture content within the range of 20% to 80% by weight, mixing the wet mix to provide a coherent workable protein-containing dough, and thereafter subjecting the coherent workable protein dough to non-turbulent stretching and heat to provide unidirectional parallel meat-like fibers. A meat-like vegetable protein-containing product is made having unidirectional parallel fiber structure similar to that of natural meat fiber structure. The protein mix can contain up to 50% of fat, which would be at least partially replaced by sucrose polyester in the present invention.

U.S. Pat. No. 4,001,441 to Liepa discloses another preferred process for making meat analogs. The process comprises forming a dry protein mix, adjusting the moisture content of the dry mix to form a dough-like protein wet mix, sheeting the protein wet mix to form a coherent workable protein dough sheet, cutting the sheet to form fiber-like strands, aggregating the strands into a desired fiber alignment, preferably coating the aligned fibers with an edible binder material, and stabilizing the fibers to form a coherent fiber mass closely resembling meat in appearance, texture, and eating quality. Prior to stabilization, fat can be added to the fiber-like strands. A portion of the fat would be replaced by sucrose polyester in the present invention.

Another preferred process for making meat analogs is described in U.S. Pat. 3,840,679 to Liepa et al. The process comprises forming a dry protein mix, adjusting the moisture content of the dry mix to form a dough-like protein wet mix, creping the protein wet mix to form a coherent workable creped protein dough sheet, aggregating the creped sheet, preferably coating the aggregate with an edible binder material, and stabilizing the aggregate to form a coherent fiber mass closely resembling meat in appearance, texture, and eating quality. In another embodiment the original mix is a dry fiber mix comprised of starches and/or gums. Fat can be added to the creped sheet in an additional step prior to stabilization.

U.S. Pat. No. 4,447,461 to Loos et al. discloses preferred meat analog-containing spaghetti sauces. The sauces are organoleptically superior to the same sauces containing real meat because the protein particles have a superior particle size distribution rather than a uniform size. The meat analog is prepared by (1) extrusion cooking soy concentrate to prepare an extrudate; (2) comminution of the extrudate; (3) mixing the resulting extrudate with a water slurry of binder; (4) frying the mixture in edible fat or oil to produce an agglomerate mat; and (5) sizing the agglomerate mat to produce a finished analog having the preferred particle size distribution when removed from the sauce in which it is mixed for consumption. In the present invention, the mixture would be fried in sucrose polyester. The preferred particle size distribution is: (a) all particles through a 15.9 mm screen; (b) about 14% on a 12.7 mm screen; (c) about 15% on a 9.51 mm screen; (d) about 33% on a 5.66 mm screen; (e) about 30% through a 4.76 mm screen; and the balance on a 4.76 mm screen.

A preferred meat analog product resembling comminuted meat, for example, hamburger, in both texture and appearance, can be made by a process comprising the steps of extruding a vegetable protein having at least 40% protein and from 10% to 40% added water under conditions such that the temperature of the extrudate as it emerges from the extruder is less than 352° F. (178° C.); water-washing the extrudate at temperatures of from 149° F. (65° C.) to 208° F. (98° C.); removing the excess water from the extrudate so that the final extrudate has at least 60% water; and mixing the hydrated extrudate with an aqueous dispersion of heat-coagulable protein to form a meat analog agglomerate. The agglomerate is heated to coagulate the protein. Microwave heating is a preferred way of coagulating the protein in an analog containing sucrose polyester. In the event that the extrudate is prepared with a twin screw extruder, the water washing and water removal steps may be omitted and replaced by hydrating the extrudate with the desired level of added moisture. The sucrose polyester can be added to the agglomerate prior to heat coagulation, or it can be used as a frying fat to heat coagulate the protein.

The food compositions of the present invention can also contain animal proteins in addition to the vegetable protein. These include proteins such as those derived from milk, poultry, meat, and/or fish.

D. The Sucrose Polyester

The present food compositions contain at least 1 gram of a particular kind of sucrose fatty acid ester. The sucrose fatty acid ester must have at least four fatty acid ester groups. Sucrose fatty acid ester compounds that contain three or less fatty acid ester groups are digested in and the products of digestion are absorbed from the intestinal tract much in the manner of ordinary triglyceride fats, whereas sucrose fatty acid ester compounds that contain four or more fatty acid ester groups are substantially non-digestible and consequently non-absorbable by the human body. It is not necessary that all of the hydroxyl groups of the sucrose be esterified with fatty acid, but it is preferable that the sucrose contain no more than three unesterified hydroxyl groups, and more preferable that it contain no more than two unesterified hydroxyl groups. Most preferably, substantially all of the hydroxyl groups of the sucrose are esterified with fatty acid, i.e., the compound is substantially completely esterified. The fatty acids esterified to the sucrose molecule can be the same or mixed.

The fatty acids groups esterified to the sucrose molecule must contain from about 8 to about 22 carbon atoms, and preferably from about 14 to about 18 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers.

The sucrose fatty acid polyesters suitable for use herein can be prepared by a variety of methods known to those skilled in the art. These methods include: transesterification of the sucrose with methyl, ethyl or glycerol fatty acid esters using a variety of catalysts; acylation of the sucrose with a fatty acid chloride; acylation of the sucrose with a fatty acid anhydride; and acylation of the sucrose with a fatty acid, per se. As an example, the preparation of sucrose fatty acid esters is described in U.S. Pat. Nos. 2,831,854, 3,963,699, 4,517,360 and 4,518,772 (all herein incorporated by reference).

Highly preferred sucrose polyesters of the present invention have a non-Newtonian pseudoplastic rheology at 100° F. (37.8° C.). In particular, the sucrose polyesters have, at 100° F. (37.8° C.): (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$; (b) a yield point of at least about 2,500 dynes/cm$^2$; (c) a thixotropic area of at least about $0.20 \times 10^6$ dynes/cm$^2$-sec.; and (d) a liquid/solid stability of at least about 50%.

Viscosity, yield point, the thixotropic area are well known rheological properties, and can be measured by use of an instrument such as a plate and cone viscometer (e.g., a Ferranti-Shirley viscometer, manufactured by Ferranti Electric, Inc., 87 Modular Ave., Commack, NY 11725). The basics of rheology are discussed in Idson, "Rheology: Fundamental Concepts," Cosmetics and Toiletries, Vol. 93, pp. 23–30 (July 1978), incorporated by reference herein. "Viscosity" is a measure of the internal friction resisting the movement of each layer of fluid as it moves past an adjacent layer of fluid. The "yield value" is the amount of shearing stress that must be applied before a material will begin to flow. Idson defines "thixotropy" as a reversible gel-sol-gel transition caused by the building up of a definite structure within the material. The gelled structure upon shaking or stirring becomes a sol, which when allowed to remain undisturbed, becomes gelled again.

To measure viscosity, yield point, and thixotropic area of a sample of the sucrose polyester of this invention, a plate and cone viscometer is used to record a rheogram, which is a plot of shear stress versus shear rate. Viscosity and yield point are calculated from points on the rheogram curve, and the thixotropic area is the area within the curve (also known as the "hysteresis loop"). Additional details are provided below under the Analytical Methods section.

Preferably, at 100° F. (37.8° C.) the sucrose polyesters of this invention have a viscosity of at least about 5 poise at a shear rate of 800 seconds$^{-1}$, a viscosity of at least about 20 poise at a shear rate of 100 seconds$^{-1}$, and a viscosity of at least about 200 poise at a shear rate of 10 seconds$^{-1}$. The preferred yield point of the sucrose polyesters is at least about 5,000 dynes/cm$^2$, and the preferred thixotropic area is at least about $0.75 \times 10^6$ dynes/cm$^2$-sec. Preferably, the sucrose polyesters have a liquid/solid stability of at least about 90%.

Most preferably, at 100° F. (37.8° C.) the sucrose polyesters have a viscosity of at least about 8 poise at a shear rate of 800 seconds$^{-1}$, a viscosity of at least about 30 poise at a shear rate of 100 seconds$^{-1}$, and a viscosity of at least about 400 poise at a shear rate of 10 seconds$^{-1}$. The most preferred yield point of the sucrose polyesters is at least about 15,000 dynes/cm$^2$, and the most preferred thixotropic area is at least about $1.00 \times 10^6$ dynes/cm$^2$-sec.

The preferred upper limit of the viscosity of the sucrose polyesters of this invention is about $1 \times 10^5$ poise at a shear rate of 10 seconds$^{-1}$, and about 1,000 poise at a shear rate of 100 seconds$^{-1}$. The preferred sucrose polyesters must have pseudoplastic flow properties as defined herein.

Iodine Value is a measure of the degree of unsaturation of fatty acids. The sucrose polyesters of this invention preferably have an Iodine Value of from about 36 to about 55.

The Solid Fat Content value (SFC) provides a reasonable approximation of the percent by weight solids of a particular fatty material at a given temperature. The present sucrose polyesters preferably have a Solid Fat Content at 100° F. (37.8° C.) of at least about 5%. Most preferably, the Solid Fat Content at 100° F. (37.8° C.) is at least about 10%. The sucrose polyesters preferably have a complete melting point higher than about 98.6° F. (37° C.).

Preferred sucrose fatty acid polyesters have the majority of their hydroxyl groups esterified with fatty acids. Preferably at least about 85%, and most preferably at least about 95%, of the sucrose fatty acid polyesters are selected from the group consisting of octaesters, heptaesters and hexaesters, and mixtures thereof. Preferably, no more than about 35% of the polyesters are hexaesters or heptaesters, and at least about 60% of the polyesters are octaesters. Most preferably, at least about 70% of the polyesters are octaesters.

In order to prove the desired physical properties, the sucrose fatty acid polyesters of this invention are preferably esterified with particular kinds of fatty acids. Preferably, at least about 80%, and most preferably at least about 90%, of the fatty acids are selected from the group consisting of mixtures of palmitic, stearic, oleic, linoleic, and behenic acids.

More specifically, the following is a preferred fatty acid composition: from about 9% to about 12% palmitic; from about 35% to about 53% stearic; from about 19% to about 43% oleic; from about 2% to about 17% linoleic; from about 0% to about 2% linolenic; from about 0% to about 2% arachidic; from about 0% to about 10% behenic; and from about 0% to about 2% erucic.

The following fatty acid composition is most preferred: from about 9% to about 12% palmitic; from about 42% to about 53% stearic; from about 19% to about 39% oleic; from about 2% to about 17% linoleic; from about 0% to about 2% linolenic; from about 0% to about 2% arachidic; from about 0% to about 10% behenic; and from about 0% to about 2% erucic.

Any remaining fat ingredients in the present compositions will comprise triglyceride fats or other lipid or lipid-like materials. The other fat ingredients can be noncaloric or reduced calorie fats, such as branched chain fatty acid tiglycerides, triglycerol ethers, polycarboxylic acid esters, sucrose polyethers, neopentyl alcohol esters, silicone oils/siloxanes, and dicarboxylic acid esters. Other useful fat-like materials are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

E. Additional Ingredients

The food compositions of the present invention can contain other ingredients in addition to those mentioned above. For example, they can be fortified with vitamins and minerals, particularly the fat-soluble vitamins. The fat-soluble vitamins include Vitamin A, Vitamin D, Vitamin E (tocopherol), and Vitamin K. Four different tocopherols have been identified (alpha, beta, gamma and delta), all of which are oily, yellow liquids, insoluble in water but soluble in fats and oils. The present food compositions preferably contain about 1.1 mg. of Vitamin E as d-alpha tocopheryl acetate per 1000 grams of sucrose polyester.

Vitamins that are nonsoluble in fat can similarly be included in the present food compositions. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present food compositions.

In the appropriate food compositions, an extra calorie reduction can be achieved by the use of noncaloric or reduced calorie sweeteners in the foods alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

Bulking or bodying agents are useful in many of the food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, maltodextrins, polyols, including sugar alcohols, e.g. sorbitol and mannitol, and carbohydrates, e.g., lactose.

Similarly, the present food compositions can contain dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

ANALYTICAL METHODS

I. Rheology Measurements of the Sucrose Polyester

A. Sample Preparation

The sucrose polyester is heated until it completely melts and is thoroughly mixed. Ten grams of the melted sample is weighed into a preheated 20 ml glass vial. The sample is then allowed to recrystallize at 100° F.±5° F. (37.8° C.±3° C.) for 24 hours. After the 24 hour time period has elapsed, the sample is taken to the viscometer and the viscosity, yield point and thixotropic area are measured.

B. Ferranti-Shirley Viscometer Operation Procedure

A Ferranti-Shirley viscometer equipped with a 600 g torque spring is used for the viscosity, yield point, and thixotropic area measurements. A cone is put into place, and the viscometer temperature is adjusted to 100° F. (37.8° C.). The chart recorder is calibrated, and the gap between the cone and plate is set. The cone speed is checked, and the cone and plate temperatures are equilibrated to 100° F. (37.8° C.). The panel controls are set. Sufficient sample is placed between the plate and the cone so that the gap is completely filled. The temperature is allowed to stabilize at 100° F. (37.8° C.) for about 30 seconds, and then the cone rotation and recording are started. A rheogram for the sucrose polyester is recorded and analyzed to determine the viscosity, yield point, and thixotropic area. Viscosity is measured at shear rates of 800 seconds$^{-1}$, 100 seconds$^{-1}$, and 10 seconds$^{-1}$, after 10 minutes of steady shear.

II. Liquid/Solid Stability Measurement of the Sucrose Polyester

A sample is heated until it completely melts and is thoroughly mixed. The sample is then poured into Beckman #344062 4.4 ml tubes to capacity. The tubes are immediately transferred to a 100° F.±5° F. (37.8° C.±3° C.) constant temperature room and allowed to recrystallize undisturbed for 24 hours. The samples are then centrifuged at 60,000 rpm for one hour at 100° F. (37.8° C.). The force on the samples is 486,000 g's. The percent liquid separated is then measured by comparing the relative heights of the liquid and solid phases.

III. Solid Fat Content Measurement

Before determining SFC values, the sucrose polyester sample is heated to a temperature of 158° F. (70° C.) or higher for at least 0.5 hours or until the sample is completely melted. The melted sample is then tempered at a temperature of 40° F. (4.4° C.) for at least 72 hours. After tempering, the SFC value of the sample at a temperature of 100° F. (37.8° C.) is determined by pulsed nuclear magnetic resonance (PNMR). The method for determining SFC values of a fat material by PNMR is described in Madison and Hill, *J. Amer. Oil. Chem. Soc.*, Vol. 55 (1978), pp. 328-31 (herein incorporated by reference).

IV. Cholesterol and Triglyceride Measurements

Total plasma cholesterol, low density lipoprotein (LDL) cholesterol, high density lipoprotein (HDL) cholesterol, and plasma triglycerides are measured according to the methods described in *Lipid Research Clinics Program Manual of Laboratory Operations,* Washington, D.C., U.S. Government Printing Office, 1974, Volume 1, incorporated by reference herein.

V. Fat and Protein Content

The fat content and protein content of foods are disclosed in *Composition of Foods, Raw, Processed, Prepared,* USDA Handbook No. 8, Washington, D.C. (1976–1982), incorporated by reference herein. The determination of sucrose polyester in foods is accomplished by high performance liquid chromatography (HPLC). The method used to measure the fat and protein contents of foods varies with the type of food. Methods for numerous foods are disclosed in *Official Methods of Analysis of the Association of Official Analytical Chemists,* 14th Ed., 1984, published by Association of Official Analytical Chemists, Inc., Arlington, Va., these methods incorporated by reference herein. For example, methods for measuring the protein content of meat are disclosed at sections 24.028–24.040; baked products at 14.103 and 14.118; cheese at 16.274; grains at 14.067; ice cream and frozen desserts at 16.314 and 16.315; macaroni products at 14.136 and 14.137; an milk at 16.036–16.050 and 16.083. Methods for measuring the fat content of bread are disclosed at section 14.104; butter at 16.232, 16.233, 16.236 and 16.241; cocao products at 13.031–13.045; cheese at 16.284–16.286; flour at 14.019, 14.021, 14.033 and 14.034; foods in general at 43.275; ice cream and frozen desserts at 16.316 and 16.317; macaroni products at 14.134; and milk at 16.064–16.087.

The following examples are intended only to further illustrate the invention and are not intended to limit the scope of the invention which is defined by the claims.

EXAMPLE 1

An example of a suitable vegetable protein/sucrose polyester food, ground beef analog, is as follows:

|  | Ingredient | % |
|---|---|---|
| Protein Mix: | *Extrudate | 30.605 |
|  | Salt | 0.802 |
|  | Egg White Solids | 4.184 |
|  | **Beef Spice Mix | 1.030 |
|  | Beef Flavor Mix | 14.789 |
|  | Water | 47.806 |
|  | Dextrose | 0.252 |
|  | Color | 0.532 |
|  |  | 100.000 |

*Twin Screw Extruded Soy Concentrate
**Beef Spice Mix:

| Water | 0.673 |
|---|---|
| Salt | 19.350 |
| Onion Powder | 47.763 |
| Garlic Powder | 21.089 |
| Basil | 8.691 |
| Oregano | 1.251 |
| Thyme | 1.183 |
|  | 100.000 |

Mixing Conditions

All ingredients from the protein mix, except egg white solids, are hydrated in a Hobart bowl using 190° F. (88° C.) water. Mixture is cooled to 100° F. (38° C.), then egg white solids are blended in a wet mixture.

A melted sucrose polyester is added to the wet agglomerate after blending in the egg white solids in the following ratio:

Wet Protein Mix: 83.3%
Sucrose Polyester: 16.7%

Heat Set Conditions

Agglomerate is placed on a fiber glass screen at a depth of ½ inch thick. A second screen is placed on top of the agglomerate, then placed in a microwave oven.

The oven is a Panasonic with carousel. The 200 g batch is cooked two minutes and ten seconds on each side using the Medium Heat heating setting—cooked for a final yield of 84.0%.

EXAMPLE 2

An oriental beef entree (5 servings) is prepared as follows:

| Ingredient | Amount (gms.) |
|---|---|
| Water | 634 |
| Beef analog | 500 |
| Rice, boiled without salt | 350 |
| Celery, sliced diagonally | 296 |
| Mushrooms, fresh, sliced | 287 |
| Green onions, sliced | 262 |
| Bean sprouts, drained and rinsed | 250 |
| Red bell pepper, 1¼" × 1¼" | 198 |
| Green bell pepper, 1¼" × 1¼" | 147 |
| Water chestnuts, julienne | 127 |
| Light soy sauce | 50 |
| Food starch | 28 |
| Ginger, ground | 1.5 |
| Caramel color | 1.1 |
| Beef flavor | 0.38 |

The beef analog is made from soy protein by the method described in Example 1.

Procedure

In a large mixing bowl place bean sprouts, mushrooms, green onions, celery, red and green pepper and water chestnuts. Combine thoroughly; set aside. In a sauce kettle, place water. Combine soy sauce with starch, ginger, caramel color and beef flavor. Whisk together and gradually whisk into the water. Bring water to a boil, agitating constantly, until sauce thickens and becomes translucent. Pour sauce over vegetables and combine well. Serve the sauce the vegetables with cooked rice and analog.

The entree contains the following per serving: 318 kcal., 23 g. vegetable protein, 3 g. animal protein, 18 g. sucrose polyester, 3 g. fat, 47 g. carbohydrates, and 0 mg. cholesterol.

EXAMPLE 3

A peanut butter composition is prepared by intimately blending together a mixture of the following ingredients:

| Ingredients | Parts by Weight % |
|---|---|
| Finely ground roasted peanuts with 52% oil | 69.93 |
| Finely ground roasted peanuts with 16% oil | 11.47 |
| Sucrose polyester (as in Claim 5) | 10.00 |

-continued

| Ingredients | Parts by Weight % |
|---|---|
| Emulsifier | 0.70 |
| Sugar (12X) | 5.8 |
| Salt | 1.20 |
| Peanut oil | 0.40 |
| Molasses | 0.50 |

The ingredients are heated to 165° F. (74° C.), placed in a Waring Blender and blended until smooth (about 2 minutes at Grate setting), placed into a sealed container, stored at −10° F. (−23° C.) overnight, and then stored at 85° F. (29° C.) for one day prior to normal storage and use.

The serving size is 32 grams (2 tablespoons). The peanut butter contains 3.2 g. sucrose polyester per serving and 9 g. vegetable protein per serving.

EXAMPLE 4

A frozen dessert which has the texture and appearance similar to commercial ice cream is prepared as follows: 116 g. of triglycerol monostearate is melted with 5.8 g. of stearic acid soap by heating to a temperature of 219° F. (104° C.). This melt is then placed in a stainless steel beaker with 1180 g. of high fructose corn syrup, 581 g. of sucrose and 265 g. of water. This mixture has a temperature of 140° F. (60° C.) and is subjected to high shear. The sheared mix is an emulsifier-water dispersion. Then 629 g. of a triglyceride oil (Crisco Oil from The Procter & Gamble Company), which contains 174 g. of propylene glycol monostearate, and 300 g. of a sucrose polyester (I.V.=107) are heated to 122° F. (50° C.) and blended in the emulsifier-water dispersion and subjected to additional high shear. The resulting emulsion is then cooled to 90° F. (32° C.) and a bourbon vanilla flavor is added with additional high shear. 73 g. of this emulsion is blended in a home mixer running at high speed with 194 g. of milk and 51 g. of a dry mix which contains 21 g. of sucrose, 2.2 g. of dextrose, 5.85 g. of tapioca starch, 20.9 g. of soy protein isolate, 0.05 g. of coloring agent and 1.0 g. of stabilizing system which contains 0.4 g. of carboxymethyl cellulose (9M31F from Hercules Chemical Co.), 0.1 g. of citric acid, 0.2 g. of tetrasodium pyrophosphate, 0.2 g. of hydroxypropyl cellulose (Klucel variety MF from Hercules Chemical Co.), 0.1 g. of Lambda Carrageenan gum (Viscarin 402 from Marine Colloids Co.). The resulting aerated mixture has a density of about 0.31 specific gravity. The aerated mixture is then placed in a freezing compartment of a refrigerator at a temperature of about 32° F. (0° C.) for about 7 hours.

The dessert contains 133 g. per serving, of which 2.7 g. is animal protein, 6.1 g. is soy protein, and 2.8 g. is sucrose polyester. The soy protein makes up 69% of the total protein.

EXAMPLE 5

Plasma cholesterol and triglyceride lowering and high density lipoprotein retention is shown in gerbils, an experimental animal whose serum lipid response to diet is similar to humans. The gerbils are fed a hypercholesterolemic diet to which vegetable protein and sucrose polyester are added. The diet is made hypercholesterolemic by the addition of cholesterol and saturated fats.

This example illustrates the plasma lipid effects of combinations of soy protein and sucrose polyester. Plasma samples are obtained from young gerbils after three weeks of consuming hyperlipidemic diets formulated to contain the same amount of cholesterol, fat, and P/S ratio but different combinations of casein-soy-sucrose polyester.

The beneficial effects on plasma lipids are shown in the following Table 4:

TABLE 4

| Soy: Casein | Sucrose Polyester (%) | Total Cholesterol (mg./dl.) | Triglycerides (mg./dl.) | HDL/ Total Cholesterol |
|---|---|---|---|---|
| 0:100 | 0 | 180 | 110 | 0.29 |
| 50:50 | 0 | 158 | 94 | 0.37 |
| 0:100 | 2.5 | 153 | 66 | 0.33 |
| 50:50 | 2.5 | 121 | 43 | 0.42 |

It can be seen that the combination of a 50:50 ratio of soy protein to casein (animal protein) and 2.5% dietary level of sucrose polyester greatly reduces total plasma cholesterol and triglycerides, while selectively retaining high density lipoprotein.

What is claimed is:

1. A fat-containing and protein-containing food composition comprising fat ingredients, protein ingredients, and non-fat and non-protein ingredients; wherein at least 1 gram per serving of the total fat consists essentially of a substantially non-digestible, non-absorbable sucrose fatty acid ester having at least 4 fatty acid ester groups, each fatty acid having from about 8 to about 22 carbon atoms; wherein at least 1.5 grams per serving (by protein content) of the total protein comprises vegetable protein; and wherein the ratio of vegetable protein to sucrose fatty acid ester is at least 1.25 to 1.

2. A food composition according to claim 1 wherein at least 3 grams per serving of the total fat consists essentially of the sucrose fatty acid ester.

3. A food composition according to claim 2 wherein at least 5 grams per serving of the total fat consists essentially of the sucrose fatty acid ester.

4. A food composition according to claim 3 wherein from 5 grams to about 20 grams per serving of the total fat consists essentially of the sucrose fatty acid ester.

5. A food composition according to claim 1 wherein at least 4.5 grams per serving of the total protein comprises vegetable protein.

6. A food composition according to claim 5 wherein at least 8 grams per serving of the total protein comprises vegetable protein.

7. A food composition according to claim 5 wherein the ratio of vegetable protein to sucrose fatty acid ester is at least 1.35 to 1.

8. A food composition according to claim 1 wherein the sucrose fatty acid ester has, at 100° F. (37.8° C.):
  (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$;
  (b) a yield point of at least about 2,500 dynes/cm$^2$;
  (c) a thixotropic area of at least about $0.20 \times 10^6$ dynes/cm$^2$-sec.; and
  (d) a liquid/solid stability of at least 50%.

9. A food composition according to claim 1 wherein the vegetable protein is selected from the group consisting of soy protein, wheat gluten, peanut protein, glandless cottonseed protein, yeast protein, and mixtures thereof.

10. A food composition according to claim 1 wherein the composition is a meat analog.

11. A food composition according to claim 1 wherein the composition is a nut spread.

12. A food composition according to claim 1 wherein the composition is a dairy-type product.

13. A food composition according to claim 12 wherein the composition is a frozen dairy dessert.

14. A food composition according to claim 1 wherein the composition is a baked good.

15. A food composition according to claim 1 wherein the composition is imitation cheese.

16. A food composition according to claim 1 wherein the composition is imitation nuts.

17. A food composition according to claim 1 wherein the composition is tofu.

18. A food composition according to claim 10 wherein the meat analog is prepared by a process which comprises forming a dry protein mix, adjusting the moisture content of the dry mix to form a dough-like protein wet mix, sheeting the protein wet mix to form a coherent workable protein dough sheet, cutting the sheet to form fiber-like strands, aggregating the strands into a desired fiber alignment, coating the aligned fibers with an edible binder material, adding a fat containing sucrose polyester to the strands, and stabilizing the fibers to form a coherent fiber mass closely resembling meat in appearance, texture, and eating quality.

19. A food composition according to claim 10 wherein the meat analog is prepared by a process which comprises the steps of extruding a vegetable protein having at least 40% protein and from 10% to 40% added water under conditions such that the temperature of the extrudate as it emerges from the extruder is less than 178° C.; water-washing the extrudate at temperatures of from 65° C. to 98° C.; removing the excess water from the extrudate so that the final extrudate has at least 60% water; mixing the hydrated extrudate with an aqueous dispersion of heat-coagulable protein to form a meat analog agglomerate; and heating the agglomerate to coagulate the protein.

20. A method for lowering plasma cholesterol levels comprising administering to a human susceptible to or afflicted with hypercholesterolemia food compositions comprising fat ingredients, protein ingredients, and non-fat and non-protein ingredients; wherein at least 1 gram per serving of the total fat consists essentially of a substantially non-digestible, non-absorbable sucrose fatty acid ester having at least 4 fatty acid ester groups, each fatty acid having from about 8 to about 22 carbon atoms; wherein at least 1.5 grams per serving (by protein content) of the total protein comprises vegetable protein; wherein the ratio of vegetable protein to sucrose fatty acid ester is at least 1.25 to 1; and wherein the compositions are administered to provide at least about 0.5% sucrose fatty acid ester in the daily diet (dry weight basis) and a daily dietary ratio of vegetable protein to animal protein of at least about 50:50.

21. A method according to claim 20 wherein the compositions are administered to provide at least about 2.5% sucrose fatty acid ester in the daily diet (dry weight basis).

22. A method according to claim 20 wherein the level of high density lipoprotein in the plasma is maintained while the level of total cholesterol is lowered.

23. A method of lowering plasma triglyceride levels comprising administering to a human susceptible to or afflicted with hyperlipidemia food compositions comprising fat ingredients, protein ingredients, and non-fat and non-protein ingredients; wherein at least 1 gram per serving of the total fat consists essentially of a substantially non-digestible, non-absorbable sucrose fatty acid ester having at least 4 fatty acid ester groups, each fatty acid having from about 8 to about 22 carbon atoms; wherein at least 1.5 grams per serving (by protein content) of the total protein comprises vegetable protein; wherein the ratio of vegetable protein to sucrose fatty acid ester is at least 1.25 to 1; and wherein the compositions are administered to provide at least about 0.5% sucrose fatty acid ester in the daily diet (dry weight basis) and a daily dietary ratio of vegetable protein to animal protein of at least about 50:50.

24. A method according to claim 23 wherein the compositions are administered to provide at least about 2.5% sucrose fatty acid ester in the daily diet (dry weight basis).

* * * * *